(12) United States Patent
Hsu et al.

(10) Patent No.: US 6,562,368 B2
(45) Date of Patent: *May 13, 2003

(54) TRANSDERMAL ADMINISTRATION OF OXYBUTYNIN USING HYDROXIDE-RELEASING AGENTS AS PERMEATION ENHANCERS

(75) Inventors: Tsung-Min Hsu, San Diego, CA (US); Eric C. Luo, Plano, TX (US)

(73) Assignee: Dermatrends, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/737,828

(22) Filed: Dec. 14, 2000

(65) Prior Publication Data

US 2001/0031787 A1 Oct. 18, 2001

Related U.S. Application Data

(63) Continuation-in-part of application No. 09/569,889, filed on May 11, 2000, which is a continuation-in-part of application No. 09/465,098, filed on Dec. 16, 1999.

(51) Int. Cl.⁷ ......................... A61F 13/00; A61F 13/02; A61L 15/00; A61L 15/16
(52) U.S. Cl. .................. 424/449; 424/443; 424/445; 424/447; 424/448; 514/946; 514/947; 514/944
(58) Field of Search .................. 424/449, 443, 424/448; 514/818, 821, 906, 929, 310, 617, 946

(56) References Cited

U.S. PATENT DOCUMENTS

| | | | |
|---|---|---|---|
| 4,789,547 A | 12/1988 | Song et al. | |
| 4,837,027 A | 6/1989 | Lee et al. | |
| 5,071,657 A | 12/1991 | Oloff et al. | |
| 5,432,192 A | 7/1995 | Sawanishi et al. | |
| 5,446,070 A | 8/1995 | Mantelle | |
| 5,462,744 A | 10/1995 | Gupte et al. | |
| 5,462,746 A | 10/1995 | Wolter et al. | |
| 5,474,783 A | 12/1995 | Miranda et al. | |
| 5,498,417 A | 3/1996 | Lhila et al. | |
| 5,500,222 A * | 3/1996 | Lee et al. | 424/448 |
| 5,532,278 A * | 7/1996 | Aberg et al. | 424/449 |
| 5,534,496 A | 7/1996 | Lee et al. | |
| 5,562,917 A | 10/1996 | Durif et al. | |
| 5,573,778 A | 11/1996 | Therriault et al. | |
| 5,599,554 A | 2/1997 | Majeti | |
| 5,614,211 A | 3/1997 | Gale et al. | |
| 5,674,895 A | 10/1997 | Guittard et al. | |
| 5,807,568 A | 9/1998 | Cody et al. | |
| 5,830,497 A * | 11/1998 | Yamanaka et al. | 424/448 |
| 5,834,513 A | 11/1998 | Ptchelintsev et al. | |
| 5,847,003 A | 12/1998 | Ptchelintsev et al. | |
| 5,879,690 A | 3/1999 | Perricone | |
| 5,939,094 A | 8/1999 | Durif et al. | |
| 5,962,018 A | 10/1999 | Curtis et al. | |
| 5,985,317 A | 11/1999 | Venkateshwaran et al. | |
| 5,989,586 A | 11/1999 | Hsu et al. | |
| 5,990,113 A | 11/1999 | Yamazaki et al. | |
| 5,993,851 A | 11/1999 | Foldvari | |
| 6,019,988 A * | 2/2000 | Parab et al. | 424/400 |
| 6,019,997 A | 2/2000 | Scholz et al. | |
| 6,123,961 A | 9/2000 | Aberg | |
| 6,174,546 B1 | 1/2001 | Therriault et al. | |
| 6,197,331 B1 * | 3/2001 | Lerner et al. | 424/443 |
| 6,204,268 B1 | 3/2001 | Scarborough et al. | |
| 6,207,184 B1 * | 3/2001 | Ikeda et al. | 424/443 |
| 6,316,011 B1 * | 11/2001 | Ron et al. | 424/401 |

FOREIGN PATENT DOCUMENTS

| | | |
|---|---|---|
| EP | 0709088 | 5/1996 |
| FR | 2692145 | 12/1993 |
| JP | 2180835 | 7/1990 |
| WO | WO 99/49844 | 10/1999 |

OTHER PUBLICATIONS

U.S. patent application Ser. No. 09/465,098, Luo et al., filed Dec. 16, 1999.
U.S. patent application Ser. No. 09/569,889, Luo et al., filed May 11, 2000.

* cited by examiner

Primary Examiner—Thurman K. Page
Assistant Examiner—Isis Ghali
(74) Attorney, Agent, or Firm—Dianne E. Reed; Shelley P. Eberle; Reed & Eberle LLP

(57) ABSTRACT

A method is provided for increasing the permeability of skin or mucosal tissue to transdermally administered oxybutynin. The method involves use of a specified amount of a hydroxide-releasing agent, the amount optimized to increase the flux of the drug through a body surface while minimizing the likelihood of skin damage, irritation or sensitization. Formulations, drug delivery systems and methods of treatment are provided as well.

47 Claims, No Drawings

TRANSDERMAL ADMINISTRATION OF OXYBUTYNIN USING HYDROXIDE-RELEASING AGENTS AS PERMEATION ENHANCERS

CROSS-REFERENCE TO RELATED APPLICATIONS

This is a continuation-in-part of U.S. Ser. No. 09/569,889, filed May 11, 2000 which is a continuation-in part of U.S. Ser. No. 09/465,098, filed Dec. 16, 1999, the disclosures of which are incorporated by reference.

TECHNICAL FIELD

This invention relates generally to transdermal administration of pharmacologically active agents, and more particularly relates to methods and compositions for transdermally administering oxybutynin.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration. With many drugs, the rate of permeation through the skin is extremely low.

In order to increase the rate at which a drug penetrates through the skin, then, various approaches have been followed, each of which involves the use of either a chemical penetration enhancer or a physical penetration enhancer. Physical enhancement of skin permeation include, for example, electrophoretic techniques such as iontophoresis. The use of ultrasound (or "phonophoresis") as a physical penetration enhancer has also been researched. Chemical enhancers are compounds that are administered along with the drug (or in some cases the skin may be pretreated with a chemical enhancer) in order to increase the permeability of the stratum corneum, and thereby provide for enhanced penetration of the drug through the skin. Ideally, such chemical penetration enhancers (or "permeation enhancers," as the compounds are referred to herein) are compounds that are innocuous and serve merely to facilitate diffusion of the drug through the stratum corneum.

Nevertheless, the number of drugs that can be safely and effectively administered through the skin, without concomitant problems such as irritation and sensitization, remains limited.

The present invention is directed to the transdermal administration of 4-diethylamino-2-butynyl phenylcyclohexlglycolate, or "oxybutynin." Preparation of the drug in racemic form is described in U.K. Patent No. 940,540. Oxybutynin is classified as an anticholinergic antispasmodic drug and is commonly used in treating individuals suffering from an overactive bladder, e.g., neurogenic bladder. See, for example, U.S. Pat. No. 5,674,895 to Guittard et al.

Oxybutynin has the molecular structure (I)

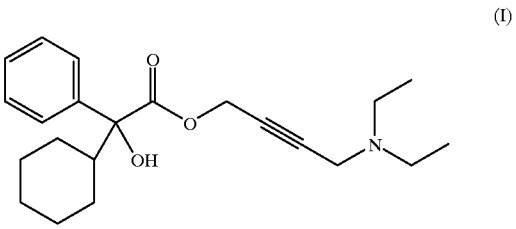

and, as may be seen, contains a chiral center. Thus, oxybutynin exists as two different isomers, as follows:

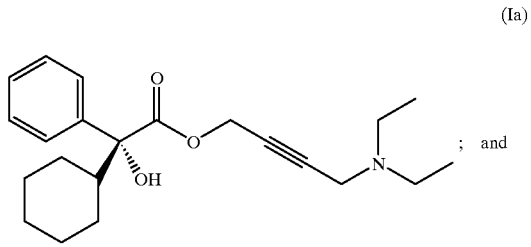

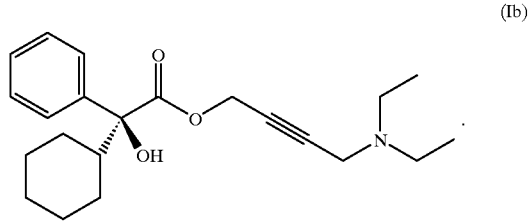

Isomer (Ia) represents the enantiomer of oxybutynin having the S absolute stereochemistry and exhibits dextrorotatory properties. Isomer (Ib) represents the enantiomer of oxybutynin having the R absolute stereochemistry and exhibits levorotatory properties. Commercially available preparations contain racemic oxybutynin in the form of the hydrochloride salt. The amount of oxybutynin in these preparations ranges from 5 mg to 30 mg per unit dose.

Current formulations of oxybutynin are administered orally, in tablet or syrup form. Conventional tablets are available that are generally taken two to three times daily. In addition, extended release tablets are also commercially available for once daily dosing. The present invention, however, is directed to the transdermal administration of oxybutynin. There are a number of advantages to administering oxybutynin transdermally: continuous delivery provides for sustained blood levels of the drug, there is no first-pass effect; side effects typically associated with oral administration may be avoided; continuous delivery provides for sustained blood levels; the transdermal patch is easily removable if any side effects do occur; and the likelihood of both patient acceptance and patient compliance is significantly improved.

Transdermal administration of oxybutynin has been proposed. U.S. Pat. No. 5,614,211 to Gale et al. describes a device for transdermally administering oxybutynin, the device comprising a special layer that eliminates blooming and delamination between the contact adhesive and drug reservoir due to migration of surfactant into other layers of the device. U.S. Pat. No. 5,500,222 to Lee et al. also describes transdermal administration of oxybutynin. In the aforementioned patent, however, a dual permeation enhancer mixture comprising lauryl acetate and a monoglyceride is required for sufficient flux of oxybutynin through the skin. U.S. Pat. No. 5,532,278 to Aberg et al. describes methods and compositions for treating urinary incontinence using optically pure (S)-oxybutynin. Although transdermal administration of (S)-oxybutynin is discussed, the patent describes transdermal systems that include only conventional permeation enhancers. Furthermore, U.S. Pat. No. 6,123,961 Aberg describes transdermal administration of (R)-oxybutynin. Permeations enhancers, however, are not mentioned. As will also be appreciated, conversion of the salt forms of oxybutynin, e.g., oxybutynin hydrochloride, is typically necessary before incorporation into a transdermal drug delivery system, since the acid addition salt exhibits even lower skin flux than the free base. See, for example, the '211 patent.

Accordingly, there is a need in the art for a way to transdermally administer oxybutynin without being limited by the drug's low skin flux.

As indicated above, various compounds for enhancing the permeability of skin are known in the art and described in the pertinent texts and literature. Compounds that have been used to enhance skin permeability include: sulfoxides such as dimethylsulfoxide (DMSO) and decylmethylsulfoxide ($C_{10}$MSO); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; organic acids, particularly salicylic acid and salicylates, citric acid and succinic acid; and certain peptides, e.g., peptides having Pro-Leu at the N-terminus and followed by a protective group (see U.S. Pat. No. 5,534,496). *Percutaneous Penetration Enhancers,* eds. Smith et al. (CRC Press, 1995) provides an excellent overview of the field and further background information on a number of chemical and physical enhancers.

Although many chemical permeation enhancers are known, there is an ongoing need for enhancers that are highly effective in increasing the rate at which a drug permeates the skin, do not result in skin damage, irritation, sensitization, or the like, and also allows neutralization of an acid addition salt such as oxybutynin hydrochloride during, rather than prior to, patch manufacture. It has now been discovered that hydroxide-releasing agents are highly effective permeation enhancers, even when used without coenhancers, and provide all of the aforementioned advantages relative to known permeation enhancers. Furthermore, in contrast to conventional enhancers, transdermal administration of drugs such as oxybutynin with hydroxide-releasing agents as permeation enhancers, employed at the appropriate levels, does not result in systemic toxicity.

SUMMARY OF THE INVENTION

It is thus a primary object of the invention to address the above-described need in the art by providing a method for transdermally administering oxybutynin in neutral, uncharged form.

It is another object of the invention to provide a method for treating conditions, disorders or diseases that are responsive to administration of oxybutynin by transdermally administering oxybutynin to a patient in need of such therapy.

It is another object of the invention to provide such a method wherein a hydroxide-releasing agent is employed as a permeation enhancer to increase the flux of oxybutynin through a patient's skin or mucosal tissue.

It is still another object of the invention to provide such a method wherein the amount of hydroxide-releasing agent employed is optimized to enhance permeation while minimizing or eliminating the possibility of skin damage, irritation or sensitization.

It is an additional object of the invention to provide formulations and drug delivery systems for carrying out the aforementioned methods.

Additional objects, advantages and novel features of the invention will be set forth in part in the description that follows, and in part will become apparent to those skilled in the art upon examination of the following, or may be learned by practice of the invention.

In one aspect of the invention, then, a method is provided for increasing the rate at which oxybutynin permeates through the body surface of a patient. The method involves administering the drug to a predetermined area of the patient's body surface in combination with a hydroxide-releasing agent in a predetermined amount effective to enhance the flux of the agent through the body surface without causing damage thereto. The predetermined amount of the hydroxide-releasing enhancer is preferably an amount effective to provide a pH at the body surface in the range of about 8.0 to 13, preferably about 8.0 to 11.5, more preferably about 8.5 to 11.5, during drug administration. If a skin patch is used, this is the preferred pH at the interface between the basal surface of the patch (i.e., the skin-contacting or mucosal-contacting surface of the patch) and the body surface. The optimal amount (or concentration) of any one hydroxide-releasing agent will, however, depend on the specific hydroxide-releasing agent, i.e., on the strength or weakness of the base, its molecular weight, and other factors as will be appreciated by those of ordinary skill in the art of transdermal drug delivery. This optimal amount may be determined using routine experimentation to ensure that the pH at the body surface is within the aforementioned ranges, i.e., in the range of about 8.0 to 13, preferably about 8.0 to 11.5, more preferably about 8.5 to 11.5. A conventional transdermal drug delivery device or "patch" may be used to administer the active agent, in which case the drug and hydroxide-releasing agent are generally present in a drug reservoir or reservoirs. However, the drug and hydroxide-releasing agent may also be administered to the body surface using a liquid or semisolid formulation. Alternatively, or in addition, the body surface may be pretreated with the enhancer, e.g., treated with a dilute solution of the hydroxide-releasing agent prior to transdermal drug administration. Such a solution will generally be comprised of a protic solvent (e.g., water or alcohol) and have a pH in the range of about 8.0 to 13, preferably about 8.0 to 11.5, and more preferably about 8.5 to 11.5.

The oxybutynin may be present in racemic form or in the form of an individual isomer. Transdermal administration of oxybutynin as provided herein is useful in treating patients suffering from urinary urgency, urinary frequency, urinary leakage, incontinence, and painful or difficult urination caused by neurogenic bladder.

In a related aspect of the invention, a composition of matter is provided for delivering oxybutynin through a body surface using a hydroxide-releasing agent as a permeation enhancer. Generally, the formulation comprises (a) a therapeutically effective amount of oxybutynin, (b) a hydroxide-releasing agent in an amount effective to enhance the flux of the oxybutynin through the body surface without causing damage thereto, and (c) a pharmaceutically acceptable carrier suitable for transdermal drug administration. The composition may be in any form suitable for application to the body surface, and may comprise, for example, a cream, lotion, solution, gel, ointment, paste or the like, and/or may be prepared so as to contain liposomes, micelles, and/or microspheres. The composition may be directly applied to the body surface or may involve use of a drug delivery device. In either case, it is preferred although not essential that water be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration.

In another aspect of the invention, a drug delivery system is provided for the transdermal administration of oxybutynin using a hydroxide-releasing agent as a permeation enhancer. The system will generally comprise: at least one drug reservoir containing oxybutynin and the hydroxide-releasing agent in an amount effective to enhance the flux of the drug through the body surface without causing damage thereto; a means for maintaining the system in drug and enhancer transmitting relationship to the body surface; and a backing layer that serves as the outer surface of the device during use. The backing layer may be occlusive or nonocclusive, although it is preferably occlusive. The drug reservoir may be comprised of a polymeric adhesive, which may serve as the basal surface of the system during use and thus function as the means for maintaining the system in drug and enhancer transmitting relationship to the body surface. The drug reservoir may also be comprised of a hydrogel, or it may be a sealed pouch within a "patch"-type structure wherein the drug and hydroxide-releasing agent are present in the pouch as a liquid or semi-solid formulation. In some cases, however, e.g., with an occlusive gel, a nonaqueous formulation may be used with or without an occlusive overlayer.

DETAILED DESCRIPTION OF THE INVENTION

Definitions and Overview

Before describing the present invention in detail, it is to be understood that this invention is not limited to specific drug delivery systems, device structures, enhancers or carriers, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a hydroxide-releasing agent" includes mixtures of two or more hydroxide-releasing agents, and the like.

In describing and claiming the present invention, the following terminology will be used in accordance with the definitions set out below.

The terms "drug" or "pharmacologically active agent" or "active agent" as used herein refer to a compound or composition of matter which, when administered to an organism (human or animal) induces a desired pharmacologic and/or physiologic effect by local and/or systemic action. Also included are derivatives and analogs of those compounds or classes of compounds specifically mentioned which also induce the desired effect. The primary active agent herein is oxybutynin.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient, as the term is used herein, thus encompasses both prevention of a disorder in a predisposed individual and treatment of the disorder in a clinically symptomatic individual.

The term "hydroxide-releasing agent" as used herein is intended to mean an agent that releases free hydroxide ions in an aqueous environment. The agent may contain hydroxide ions and thus release the ions directly (e.g., an alkali metal hydroxide), or the agent may be one that is acted upon chemically in an aqueous environment to generate hydroxide ions (e.g., a metal carbonate).

By "therapeutically effective" amount is meant a nontoxic but sufficient amount of an active agent to provide the desired therapeutic effect.

By "transdermal" drug delivery is meant administration of a drug to the skin surface of an individual so that the drug passes through the skin tissue and into the individual's blood stream, thereby providing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of a topical drug or pharmacologically active agent to the skin or mucosa, as in, for example, the treatment of various skin disorders. Topical administration, in contrast to transdermal administration, provides a local rather than a systemic effect. Unless otherwise stated or implied, the terms "topical drug administration" and "transdermal drug administration" are used interchangeably.

The term "body surface" is used to refer to skin or mucosal tissue.

By "predetermined area" of skin or mucosal tissue, which refers to the area of skin or mucosal tissue through which a drug-enhancer formulation is delivered, is intended a defined area of intact unbroken living skin or mucosal tissue. That area will usually be in the range of about 5 cm$^2$ to about 200 cm$^2$, more usually in the range of about 5 cm$^2$ to about 100 cm$^2$, preferably in the range of about 20 cm$^2$ to about 60 cm$^2$. However, it will be appreciated by those skilled in the art of drug delivery that the area of skin or mucosal tissue through which drug is administered may vary significantly, depending on patch configuration, dose, and the like.

"Penetration enhancement" or "permeation enhancement" as used herein relates to an increase in the permeability of the skin or mucosal tissue to the selected pharmacologically active agent, i.e., so that the rate at which the agent permeates therethrough (i.e., the "flux" of the agent through the body surface) is increased relative to the rate that would be obtained in the absence of permeation enhancement. The enhanced permeation effected through the use of such enhancers can be observed by measuring the rate of diffusion of drug through animal or human skin using, for example a Franz diffusion apparatus as known in the art.

An "effective" amount of a permeation enhancer is meant a nontoxic, nondamaging but sufficient amount of the enhancer to provide the desired increase in skin permeability and, correspondingly, the desired depth of penetration, rate of administration, and amount of drug delivered.

"Carriers" or "vehicles" as used herein refer to carrier materials suitable for transdermal drug administration. Carriers and vehicles useful herein include any such materials known in the art which are nontoxic and does not interact with other components of the composition in a deleterious manner.

The term "aqueous" refers to a formulation or drug delivery system that contains water or that becomes water-containing following application to the skin or mucosal tissue.

The term "racemic oxybutynin" as used herein refers to a mixture of the two isomers of oxybutynin, i.e., d-oxybutynin and l-oxybutynin. Oxybutynin is generally although not necessarily administered in uncharged (electronically neutral) form, wherein the amine group of the molecule exists in free base form, i.e., containing an uncharged diethylamino group.

Accordingly, the invention pertains to a method, composition and drug delivery system for increasing the rate at which oxybutynin permeates through the body surface of a patient, wherein the method involves administering the agent to a predetermined area of the patient's body surface in combination with a hydroxide-releasing agent in an amount effective to enhance the flux of the agent through the body surface without causing damage thereto.

The Hydroxide Releasing Agent

The "hydroxide-releasing agent" is a chemical compound that releases free hydroxide ions in the presence of an aqueous fluid. The aqueous fluid may be natural moisture at the skin surface, or a patch or composition that is used may contain added water, and/or be used in connection with an occlusive backing. Similarly, any liquid or semisolid formulation that is used is preferably aqueous or used in conjunction with an overlayer of an occlusive material.

Any hydroxide-releasing agent may be used provided that the compound releases free hydroxide ions in the presence of an aqueous fluid. Examples of suitable hydroxide-releasing agents include, but are not limited to, inorganic hydroxides, inorganic oxides, and alkali metal or alkaline earth metal salts of weak acids. Inorganic hydroxides include, for example, ammonium hydroxide, alkali metal hydroxide and alkaline earth metal hydroxides, such as sodium hydroxide, calcium hydroxide, potassium hydroxide, magnesium hydroxide, and the like. Inorganic oxides include, for example, magnesium oxide, calcium oxide, and the like. Metal salts of weak acids include, for example, sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), ammonium phosphate (dibasic), and the like. Preferred hydroxide-releasing agents are metal hydroxides such as sodium hydroxide and potassium hydroxide.

It is important that the amount of hydroxide-releasing agent in any patch or formulation is optimized so as to increase the flux of oxybutynin through the body surface while minimizing any possibility of skin damage. In general, this means that the pH at the body surface in contact with a formulation or drug delivery system of the invention (i.e., the interface between the body surface and the formulation or delivery system) should be in the range of approximately 8.0 to 13, preferably about 8.0 to 11.5, more preferably about 8.5 to 11.5. This will typically although not necessarily mean that the pH of the formulation or the drug composition contained within a delivery system will be in the range of approximately 8.0 to 13, preferably about 8.0 to 11.5, more preferably about 8.5 to 11.5.

For inorganic hydroxides, the amount of hydroxide-releasing agent will typically represent about 0.5 wt. % to 4.0 wt. %, preferably about 0.5 wt. % to 3.0 wt. %, more preferably about 0.75 wt. % to 2.0 wt. % and optimally about 1.0 wt. %, of a topically applied formulation or of a drug reservoir of a drug delivery system, or "patch." The aforementioned amount applies to formulations and patches in which oxybutynin is (1) in uncharged, free base form, and where (2) there are no additional species in the formulation or patch that could react with or be neutralized by the inorganic hydroxide. For formulations when oxybutynin is present in the form of an acid addition salt, e.g., oxybutynin hydrochloride and/or wherein there are additional species in the formulations or systems that can be neutralized by or react with the hydroxide-releasing agent (i.e., acidic inactive ingredients), the amount of the inorganic hydroxide will be the total of (1) the amount necessary to neutralize or react with the drug and/or other base-neutralizable species, plus (2) about 0.5 wt. % to 4.0 wt. %, preferably about 0.5 wt. % to 3.0 wt. %, more preferably about 0.75 wt. % to 2.0 wt. % and optimally about 1.0 wt. %, of the formulation or drug reservoir to enhance the flux of the drug through the skin or mucosal tissue. For patches, the aforementioned percentages are given relative to the total dry weight of the formulation components and the adhesive, gel or liquid reservoir.

For other hydroxide-releasing agents such as inorganic oxides and metal salts of weak acids, the amount of hydroxide-releasing agent in the formulation or drug delivery system may be substantially higher, as high as about 20 wt. %, in some cases as high as about 25 wt. % or higher, but will generally be in the range of about 2 wt. % to about 20 wt. %.

Still greater amounts of hydroxide-releasing agent may be used by controlling the rate and/or quantity of release of the hydroxide-releasing agent preferably during the drug delivery period itself.

However, for all hydroxide-releasing agents herein, the optimum amount of any particular agent will depend on the strength or weakness of the base, the molecular weight of the base, and other factors such as any other acidic species in the formulation or patch. One skilled in the art may readily determine the optimum amount for any particular agent by ensuring that a formulation or drug delivery system should in all cases be effective to provide a pH at the skin surface in the range of about 8.0 to 13, preferably in the range of about 8.0 to 11.5, more preferably in the range of about 8.5 to 11.5, during application to reach the desired pH at the body surface. This in turn ensures that the degree of enhancement is optimized while the possibility of damage to the body surface is eliminated or at least substantially minimized.

The Active Agent

The active agent administered is oxybutynin in the form of a racemate or a single isomer. Although disagreement exists concerning which isomer possesses greater pharmacologic activity, several studies indicate that the activity of the racemate resides predominantly in the R enantiomer. See Noronha-Blob (1990) *J. Pharmacol. Exp. Ther.* 256(2):562–567 and Goldenberg (1999) *Clin. Ther.* 21(4):634–642.

As previously stated, U.K. Patent No. 940,540 describes the preparation of racemic oxybutynin. Synthesis of (S)-oxybutynin is also known. For example, the S enantiomer may be obtained by resolution of the intermediate mandelic acid followed by esterification. See Kachur et al. (1988) *J. Pharmacol. Exp. Ther.* 247(3):867–72. The R enantiomer may obtained by first preparing 4-diethylamino-2-butynyl chloride from dichlorobutyne followed by reacting the single R enantiomer of cyclohexylphenylglycolic acid with the prepared 4-diethylamino-2-butynyl chloride to yield the R enantiomer of 4-diethylamino-2-butynyl phenylcyclohexlglycolate, i.e., (R)-oxybutynin. See U.S. Pat. No. 6,123,961 to Aberg. Alternatively, the individual isomers may be isolated from a racemic mixture of oxybutynin using techniques known in the art such as chromatography-based methods that use a chiral substrate.

When an individual enantiomer of oxybutynin is used in accordance with the invention, the enantiomer is in substantially pure form, i.e., at least 90%, more preferably 97%, and most preferably 99% of the total amount (based on weight) of oxybutynin is present as the enantiomer. Thus, for example, drug delivery systems containing substantially pure (R)-oxybutynin will have at least 90%, more preferably 97%, and most preferably 99% of the total amount of oxybutynin as the R enantiomer.

If desired, oxybutynin can be co-administered with any of a number of other active agents. These additional active agents include the broad classes of compounds normally delivered through body surfaces and membranes, including skin. In general, this includes: analgesic agents; anesthetic agents; antiarthritic agents; respiratory drugs, including antiasthmatic agents; anticancer agents, including antineoplastic drugs; anticholinergics; anticonvulsants; antidepressants such as tricyclic antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids; sympathomimetics; tranquilizers; and vasodilators including general coronary, peripheral and cerebral.

Preferred classes of active agents for coadministration with oxybutynin using the present systems and methods are, like oxybutynin, drugs commonly used in treating bladder disorders. Specific examples of preferred active agents for co-administration with oxybutynin include, but are not limited to, amitriptyline hydrochloride, atropine, biperiden, dicyclomine hydrochloride, desmopressin acetate, glycopyrrolate, imipramine hydrochloride, propantheline bromide, and tolterodine tartrate.

Formulations

The method of delivery of oxybutynin may vary, but necessarily involves application of a formulation or drug delivery system containing oxybutynin and a hydroxide-releasing agent to a predetermined area of the skin or other tissue for a period of time sufficient to provide the desired systemic effect. The method may involve direct application of the composition as an ointment, gel, cream, or the like, or may involve use of a drug delivery device. In either case, water must be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a nonaqueous formulation may be used with or without an occlusive overlayer.

Suitable formulations include ointments, creams, gels, lotions, pastes, and the like. Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: *The Science and Practice of Pharmacy*, 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see *Remington: The Science and Practice of Pharmacy* for further information.

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally although not necessarily formed from lipids, preferably charged lipids such as phospholipids. Preparation of lipidic microspheres is well known in the art and described in the pertinent texts and literature.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

It may be desirable to include a second permeation enhancer in the formulation in addition to the hydroxide-releasing agent, although in a preferred embodiment the hydroxide-releasing agent is administered without any other permeation enhancers. Any other enhancers should, like the hydroxide-releasing agent itself, minimize the possibility of skin damage, irritation and systemic toxicity. Example of suitable secondary enhancers (or co-enhancers) include, but are not limited to: ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and $C_{10}$MSO may also be used, but are less preferred. As noted earlier herein, *Percutaneous Penetration Enhancers,* eds. Smith et al. (CRC Press, 1995) provides an excellent overview of the field and further information concerning possible secondary enhancers for use in conjunction with the present invention.

The formulation may also contain irritation-mitigating additives to minimize or eliminate the possibility of skin irritation or skin damage resulting from the drug, the enhancer, or other components of the formulation. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt. %, more typically not more than about 5 wt. %, of the formulations.

The concentration of the active agent in the formulation can vary a great deal, and will depend on a variety of factors, including the disease or condition to be treated, the nature and activity of the active agent, the desired effect, possible adverse reactions, the ability and speed of the active agent to reach its intended target, and other factors within the particular knowledge of the patient and physician. Preferred formulations will typically contain on the order of about 0.5 wt. % to 50 wt. %, optimally about 1 wt. % to 30 wt. %, active agents.

Drug Delivery Systems

An alternative and preferred method involves the use of a drug delivery system, e.g., a transdermal "patch," wherein the active agent is contained within a laminated structure that is to be affixed to the skin. In such a structure, the drug composition is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, hydroxide-releasing agent, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene(polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing drug, hydroxide-releasing agent or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure includes a release liner. Immediately prior to use, this layer is removed from the device so that the system may be affixed to the skin. The release liner should be made from a drug/vehicle impermeable material, and is a disposable element which serves only to protect the device prior to application. Typically, the release liner is formed from a material impermeable to the pharmacologically active agent and the hydroxide-releasing agent, and which is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or it may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly (hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a hydroxide-releasing agent, an additional enhancer, or some other component contained in the drug delivery system.

A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5 cm$^2$ to 200 cm$^2$, preferably 5 cm$^2$ to 100 cm$^2$, more preferably 20 cm$^2$ to 60 cm$^2$. That area will vary, of course, with the amount of drug to be delivered and the flux of the drug through the body surface. Larger patches will necessary to accommodate larger quantities of drug, while smaller patches can be used for smaller quantities of drug and/or drugs that exhibit a relatively high permeation rate.

Such drug delivery systems may be fabricated using conventional coating and laminating techniques known in the art. For example, adhesive matrix systems can be prepared by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture. In general, transdermal systems of the invention are fabricated by solvent evaporation, film casting, melt extrusion, thin film lamination, die cutting, or the like. The hydroxide-releasing agent will generally be incorporated into the device during patch manufacture rather than subsequent to preparation of the device.

In a preferred delivery system, an adhesive overlayer that also serves as a backing for the delivery system is used to better secure the patch to the body surface. This overlayer is sized such that it extends beyond the drug reservoir so that adhesive on the overlayer comes into contact with the body surface. The overlayer is useful because the adhesive/drug reservoir layer may lose its adhesion a few hours after application due to hydration. By incorporating such an adhesive overlayer, the delivery system remains in place for the required period of time.

Other types and configurations of transdermal drug delivery systems may also be used in conjunction with the method of the present invention, i.e., the use of a hydroxide-releasing agent as a permeation enhancer, as will be appreciated by those skilled in the art of transdermal drug delivery. See, for example, Ghosh, *Transdermal and Topical Drug Delivery Systems* (Interpharm Press, 1997), particularly Chapters 2 and 8.

As with the topically applied formulations of the invention, the composition containing drug and hydroxide-releasing agent within the drug reservoir(s) of these laminated system may contain a number of components. In some cases, the drug and hydroxide-releasing agent may be delivered "neat," i.e., in the absence of additional liquid. In most cases, however, the drug will be dissolved, dispersed or suspended in a suitable pharmaceutically acceptable vehicle, typically a solvent or gel. Other components which may be present include preservatives, stabilizers, surfactants, and the like.

Utility

Transdermal administration of oxybutynin is useful in a variety of contexts, as will be readily appreciated by those skilled in the art. For example, the transdermal administration of oxybutynin is useful in the treatment of urinary urgency, urinary frequency, urinary leakage, incontinence, and painful or difficult urination. Generally, although not necessarily, these disorders are caused by neurogenic bladder. In addition, the present compositions and drug delivery systems are useful to administer oxybutynin to treat other conditions and disorders that are responsive to transdermal administration of oxybutynin. For example, oxybutynin may be administered transdermally to treat individuals suffering from detrusor hyperreflexia and detrusor instability.

The amount of drug present in the compositions and drug delivery systems of the invention and required to achieve an effective therapeutic result depends on many factors, such as the minimum necessary dosage of the drug for the particular indication being treated; the solubility and permeability of the carrier and adhesive layer; and the period of time for which the device will be fixed to the skin or other body surface. The minimum amount of drug is determined by the requirement that sufficient quantities of drug must be present in the device to maintain the desired rate of release over the given period of application. The maximum amount for safety purposes is determined by the requirement that the quantity of drug present cannot exceed a rate of release that reaches toxic levels. Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties.

The daily dosage administered will, of course, vary from subject to subject and depend on the particular disorder or condition, the severity of the symptoms, the subject's age, weight and general condition, and the judgment of the prescribing physician. Generally, however, a daily dosage of racemic oxybutynin using the present formulations and delivery systems will be in the range of about 1 to 20 mg over a 24-hour period. The daily dose of an individual enantiomer of oxybutynin, i.e., (S)-oxybutynin or (R)-oxybutynin, using the present formulations and delivery systems is preferably lower than the corresponding racemate dose. Specifically, it is preferred that the enantiomer dose be in the range of about 0.5 to 15 mg over a 24-hour period.

The invention accordingly provides a novel and highly effective means for increasing the flux of oxybutynin through the body surface (skin or mucosal tissue) of a human or animal. The hydroxide-releasing agents discussed herein, employed in specific amounts relative to a formulation or drug reservoir, may be used as permeation enhancers. Surprisingly, the increase in permeation is not accompanied by any noticeable tissue damage, irritation, or sensitization. The invention thus represents an important advance in the field of drug delivery.

It is to be understood that while the invention has been described in conjunction with the preferred specific embodiments thereof, the foregoing description, as well as the example that follows, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following example is put forth so as to provide those of ordinary skill in the art with a complete disclosure and description of how to make and use the materials of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are part by weight, temperature is in ° C. and pressure is at or near atmospheric.

EXAMPLE 1

An in-vitro skin permeation study was conducted using three oxybutynin HCl transdermal systems. The formulations used to prepare these systems are listed in Table 1, which include weight and weight percent of each ingredient in the formulations. The weight of sodium hydroxide (NaOH) was 0.15 g, 0.25 g, and 0.35 g for formulation #Oxy-P1, -P2, and -P3 respectively. Each formulation was coated on a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of $^{11}/_{16}$ inch. The theoretical percent weight for each ingredient after drying (calculated assuming all the volatile ingredients were completely removed during drying) is listed in Table 2.

The in-vitro permeation of oxybutynin HCl through human cadaver skin from these discs was performed using Franz-type diffusion cells with a diffusion area of 1 cm$^2$. The volume of receiver solution was 8 ml. Human cadaver skin was cut to desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

The cells were filled with 10% ethanol/90% water solution. The receiver solution was completely withdrawn and replaced with fresh ethanol/water solution at each time point. The samples taken were analyzed by an HPLC for the concentration of oxybutynin HCl in the receiver solution. The cumulative amount of oxybutynin HCl across human cadaver skin was calculated using the measured oxybutynin HCl concentrations in the receiver solutions, which were shown in Table 3.

TABLE 1

Weight and Weight Percent of Each Ingredient Based on Total Solution Weight for Three Oxybutynin HCl Transdermal Systems

|  | Oxy-P1 | Oxy-P2 | Oxy-P3 |
| --- | --- | --- | --- |
| Oxybutynin HCl | 0.5 g (6.5%) | 0.5 g (6.3%) | 0.5 g (6.2%) |
| DI water | 0.65 g (8.4%) | 0.75 g (9.5%) | 0.85 g (10.5%) |
| NaOH | 0.15 g (1.9%) | 0.25 g (3.2%) | 0.35 g (4.3%) |
| Propylene glycol | 0.3 g (3.9%) | 0.3 g (3.8%) | 0.3 g (3.7%) |
| Triton X100 | 0.1 g (1.3%) | 0.1 g (1.3%) | 0.1 g (1.2%) |
| PIB adhesive (30% solid) | 4 g (51.9%) | 4 g (50.6%) | 4 g (49.4%) |
| Methylal | 1 g (13.0%) | 1 g (12.7%) | 1 g (12.3%) |
| Heptane | 1 g (13.0%) | 1 g (12.7%) | 1 g (12.3%) |

TABLE 2

Weight and Theoretical Weight Percent of Each Ingredient in the Dried Film for Three Oxybutynin HCl Transdermal Systems

|  | Oxy-P1 | Oxy-P2 | Oxy-P3 |
| --- | --- | --- | --- |
| Oxybutynin HCl | 0.5 g (15.4%) | 0.5 g (14.9%) | 0.5 g (14.5%) |
| NaOH | 0.15 g (4.6%) | 0.25 g (7.5%) | 0.35 g (10.1%) |
| Propylene glycol | 0.3 g (9.2%) | 0.3 g (9.0%) | 0.3 g (8.7%) |
| Triton X100 | 0.1 g (3.1%) | 0.1 g (3.0%) | 0.1 g (2.9%) |
| PIB adhesive | 1.2 g (36.9%) | 1.2 g (35.8%) | 1.2 g (34.8%) |
| Methylal | 1 g (30.8%) | 1 g (29.9%) | 1 g (29.0%) |

TABLE 3

Cumulative Amount of Oxybutynin HCl across human cadaver skin for Oxybutynin HCl Transdermal Systems ($\mu$g/cm$^2$)

|  | Oxy-P1 | Oxy-P2 | Oxy-P3 |
| --- | --- | --- | --- |
| 5 hours | 691.0 | 2108.7 | 1399.5 |
| 10.5 hours | 1259.4 | 2615.9 | 1865.9 |
| 24 hours | 1747.7 | 2853.5 | 2322.8 |

The cumulative amount of oxybutynin HCl across human cadaver skin at 24 hours ranged from 1747.7 $\mu$g/cm$^2$ to 2322.8 $\mu$g/cm$^2$ when the NaOH concentration in the dried patch was increased from 4.6% to 10.1%.

We claim:

1. A method for enhancing the flux of oxybutynin through a body surface, comprising administering oxybutynin to a localized region of a human patient's body surface in combination with a hydroxide-releasing agent applied to the body surface in a predetermined amount effective to enhance the flux of the oxybutynin through the localized region of the body surface without causing damage thereto, wherein the predetermined amount of the hydroxide-releasing agent is effective to provide a pH in the range of approximately 8.0 to 13 at the localized region of the body surface, during drug administration, wherein the oxybutynin and hydroxide-releasing agent are present in a formulation and the amount of hydroxide-releasing agent in the formulation applied to the body surface is the total of (a) the amount required to neutralize any acidic species in the formulation plus (b) an amount equal to approximately 0.5 wt. % to 25.0 wt. % of the formulation.

2. The method of claim 1, wherein the pH is in the range of approximately 8.0 to 11.5.

3. The method of claim 2, wherein the pH is in the range of approximately 8.5 to 11.5.

4. The method of claim 1, wherein the body surface is skin.

5. The method of claim 1, wherein the body surface is mucosal tissue.

6. The method of claim 1, wherein the formulation is aqueous.

7. The method of claim 6, wherein the formulation has a pH in the range of approximately 8.0 to 13.

8. The method of claim 7, wherein the pH is in the range of approximately 8.0 to 11.5.

9. The method of claim 8, wherein the pH is in the range of approximately 8.5 to 11.5.

10. The method of claim 6, wherein the aqueous formulation is selected from the group consisting of a cream, a gel, a lotion, and a paste.

11. The method of claim 10, wherein the formulation is a cream.

12. The method of claim 10, wherein the formulation is a gel.

13. The method of claim 1, wherein the formulation is nonaqueous.

14. The method of claim 13, wherein the formulation is an ointment.

15. The method of claim 1, wherein the hydroxide-releasing agent releases free hydroxide ions in the presence of an aqueous fluid.

16. The method of claim 1, wherein the hydroxide-releasing agent is selected from the group consisting of inorganic hydroxides, inorganic oxides, metal salts of weak acids, and mixtures thereof.

17. The method of claim 16, wherein the hydroxide-releasing agent is an inorganic hydroxide.

18. The method of claim 17, wherein the inorganic hydroxide is selected from the group consisting of ammonium hydroxide, alkali metal hydroxides, alkaline earth metal hydroxides, and mixtures thereof.

19. The method of claim 18, wherein the inorganic hydroxide is selected from the group consisting of ammonium hydroxide, sodium hydroxide, calcium hydroxide, potassium hydroxide, magnesium hydroxide, and mixtures thereof.

20. The method of claim 19, wherein the inorganic hydroxide is sodium hydroxide.

21. The method of claim 19, wherein the inorganic hydroxide is potassium hydroxide.

22. The method of claim 16, wherein the hydroxide-releasing agent is an inorganic oxide.

23. The method of claim 22, wherein the inorganic oxide is selected from the group consisting of magnesium oxide, calcium oxide and mixtures thereof.

24. The method of claim 16, wherein the hydroxide-releasing agent is a metal salt of a weak acid.

25. The method of claim 24, wherein the hydroxide-releasing agent is selected from the group consisting of sodium acetate, sodium borate, sodium metaborate, sodium carbonate, sodium bicarbonate, tribasic sodium phosphate, dibasic sodium phosphate, potassium carbonate, potassium bicarbonate, potassium citrate, potassium acetate, dibasic potassium phosphate, tribasic potassium phosphate, dibasic ammonium phosphate, and mixtures thereof.

26. The method of claim 17, wherein the amount of inorganic hydroxide in the formulation is the total of (a) the amount required to neutralize any acidic species in the formulation plus (b) an amount equal to approximately 0.5 wt. % to 4.0 wt. % of the formulation.

27. The method of claim 26, wherein the amount of inorganic hydroxide in the formulation is the total of (a) the amount required to neutralize any acidic species in the formulation plus (b) an amount equal to approximately 0.5 wt. % to 3.0 wt. % of the formulation.

28. The method of claim 27, wherein the amount of inorganic hydroxide in the formulation is the total of (a) the amount required to neutralize any acidic species in the formulation plus (b) an amount equal to approximately 0.75 wt. % to 2.0 wt. % of the formulation.

29. The method of claim 28, wherein the amount of inorganic hydroxide in the formulation is the total of (a) the amount required to neutralize any acidic species in the formulation plus (b) an amount equal to approximately 1.0 wt. % of the formulation.

30. The method of claim 26, wherein the oxybutynin is in the form of an acid addition salt, and the amount in (a) is the amount required to neutralize the acid addition salt and other acidic species in the formulation.

31. The method of claim 26, wherein the oxybutynin is in the form of the free base.

32. The method of claim 22, wherein the formulation contains up to approximately 25 wt. % of the hydroxide-releasing agent.

33. The method of claim 32, wherein the formulation contains up to approximately 20 wt. % of the hydroxide-releasing agent.

34. The method of claim 24, wherein the formulation contains up to approximately 25 wt. % of the hydroxide-releasing agent.

35. The method of claim 34, wherein the formulation contains up to approximately 20 wt. % of the hydroxide-releasing agent.

36. The method of claim 1, wherein the oxybutynin and hydroxide-releasing agent are administered by applying a drug delivery device to the localized region of the patient's body surface thereby forming a body surface-delivery device interface, the device comprising the oxybutynin and the hydroxide-releasing agent, and having an outer backing layer that serves as the outer surface of the device during use.

37. The method of claim 36, wherein the oxybutynin and hydroxide-releasing agent are present in an adhesive, gel or liquid formulation contained within the device.

38. The method of claim 36, wherein the outer backing layer is occlusive.

39. The method of claim 36, wherein the pH at the interface is in the range of approximately 8.0 to 11.5.

40. The method of claim 39, wherein the pH at the interface is in the range of approximately 8.5 to 11.5.

41. The method of claim 1, wherein the oxybutynin is administered in combination with an additional permeation enhancer.

42. The method of claim 1, wherein the oxybutynin and hydroxide-releasing agent are administered without any additional permeation enhancer.

43. The method of claim 1, wherein the oxybutynin is in the form of an acid addition salt.

44. The method of claim 43, wherein the acid addition salt is oxybutynin hydrochloride.

45. The method of claim 1, wherein the oxybutynin is administered as the racemate.

46. The method of claim 1, wherein the oxybutynin is administered as substantially pure (R)-oxybutynin.

47. The method of claim 1, wherein the oxybutynin is administered as substantially pure (S)-oxybutynin.

* * * * *